(12) United States Patent
Conover et al.

(10) Patent No.: US 7,939,280 B2
(45) Date of Patent: May 10, 2011

(54) MARKER FOR INFLAMMATORY CONDITIONS

(75) Inventors: Cheryl A Conover, Rochester, MN (US); Antonio Bayes-Genis, Barcelona (ES); David R Holmes, Rochester, MN (US); Robert S Schwartz, Inver Grove Heights, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/785,893

(22) Filed: May 24, 2010

(65) Prior Publication Data

US 2010/0285510 A1 Nov. 11, 2010

Related U.S. Application Data

(60) Continuation of application No. 12/389,983, filed on Feb. 20, 2009, now Pat. No. 7,723,049, which is a continuation of application No. 11/516,020, filed on Sep. 5, 2006, now abandoned, which is a continuation of application No. 11/254,224, filed on Oct. 18, 2005, now abandoned, which is a continuation of application No. 11/062,400, filed on Feb. 22, 2005, now abandoned, which is a continuation of application No. 10/767,666, filed on Jan. 29, 2004, now abandoned, which is a division of application No. 10/210,339, filed on Jul. 31, 2002, now Pat. No. 6,699,675, which is a division of application No. 09/760,376, filed on Jan. 12, 2001, now Pat. No. 6,500,630.

(51) Int. Cl.
*G01N 33/53* (2006.01)
*G01N 31/00* (2006.01)

(52) U.S. Cl. ......... 435/7.21; 435/7.1; 435/7.4; 435/226; 424/130.1; 530/388.26; 530/389.1; 436/501; 436/518

(58) Field of Classification Search ........................ None
See application file for complete search history.

(56) References Cited

U.S. PATENT DOCUMENTS

| | | | |
|---|---|---|---|
| 5,039,521 A | 8/1991 | Bolton et al. | |
| 5,256,411 A | 10/1993 | Bolton et al. | |
| 5,324,502 A | 6/1994 | Green et al. | |
| 5,932,188 A | 8/1999 | Snow et al. | |
| 5,958,408 A | 9/1999 | Griffiths et al. | |
| 6,172,198 B1 | 1/2001 | Sinosich | |
| 6,331,286 B1 | 12/2001 | Dees et al. | |
| 6,500,630 B2 * | 12/2002 | Conover et al. | 435/7.94 |
| 6,699,675 B2 * | 3/2004 | Holmes et al. | 435/7.1 |
| 7,115,382 B1 * | 10/2006 | Overgaard et al. | 435/7.4 |
| 7,723,049 B2 * | 5/2010 | Conover et al. | 435/7.1 |
| 2006/0063162 A1 | 3/2006 | Deng | |

FOREIGN PATENT DOCUMENTS

| | | |
|---|---|---|
| WO | 98/43630 | 10/1998 |
| WO | 99/32620 | 7/1999 |
| WO | 00/54806 | 9/2000 |

OTHER PUBLICATIONS

Bayes-Genis et al., "Insulin-Like Growth Factor Binding Protein-4 Protease Produced by Smooth Muscle Cells Increase in the Coronary Artery After Angioplasty," *Arterioscler. Thromb. Vasc. Biol.*, 2001, 21:335-341.
Bayes-Genis et al., "Pregnancy-Associated Plasma Protein A as a Marker of Acute Coronary Syndromes," *N. Engl. J. Med.*, 2001, 345(14):1022-1029.
Bersinger et al., "The pattern of serum levels of pregnancy-associated plasma protein A (PAPP-A) during the ovulatory menstrual cycle," *Br. J. Obst. Gynecol.*, 1984, 91(12):1245-1248.
Bischof et al., "Is pregnancy-associated plasma protein A a tumor marker?" *J. Obst. Gynecol.*, 1982, 143 (4):379-381.
Burke et al., "Coronary Risk Factors and Plaque Morphology in Men with Coronary Disease Who Died Suddenly," *N. Engl. J. Med.*, 1997, 336(18):1276-1282.
Christiansen et al., "Quantification and Characterization of Pregnancy-associated Complexes of Angiotensinogen and the Proform of Eosinophil Major Basic Protein in Serum and Amniotic Fluid," *Clin. Chem.*, 2000, 46(8):1099-1105.
Cole et al., "The EBV-Hybridoma Technique and Its Application to Human Lung Cancer," *Monoclonal Antibodies and Cancer Therapy*, 1985, Alan R. Liss, Inc., pp. 77-96.
Cote et al., "Generation of human monoclonal antibodies reactive with cellular antigens," *Proc. Natl. Acad. Sci. USA*, 1983, 80:2026-2030.
Daughaday and Rotwein, "Insulin-Like Growth Factors I and II. Peptide, Messenger Ribonucleic Acid and Gene Structures, Serum, and Tissue Concentrations," *Endocrin. Rev.*, 1989, 10(1):68-91.
Dean et al., "Localization of the insulin-like growth factor system in a rat model of heart failure induced by myocardial infarction," *J. Histochem. Cytochem.*, 1999, 47(5):649-656.
DeGraba, "The role of inflammation in atherosclerosis," *Adv. Neurol.*, 2003, 92:29-42.
DeLong et al., "Comparing the Areas Under Two or More Correlated Receiver Operating Characteristic Curves: A Nonparametric Approach," *Biometrics*, 1988, 44:837-845.
de Winter et al., "Independent prognostic value of C-reactive protein and troponin I in patients with unstable angina or non-Q-wave myocardial infarction," *Cardiovasc. Res.*, 1999, 42:240-245.
Durham et al., "Regulation of Insulin-like Growth Factor Binding Protein 4 by a Specific Insulin-like Growth Factor Binding Protein 4 Proteinase in Normal Human Osteoblast-like Cells: Implications in Bone Cell Physiology," *J. Bone Min. Res.*, 1994, 9(1):111-117.
Frystyk et al., "Free insulin-like growth factors (IGF-I and IGF-II) in 1994, 348:185-191 human serum," *FEBS Lett.*, 1994, 348:185-191.
Guatelli et al., "Isothermal, in vitro amplification of nucleic acids by a multienzyme reaction modeled after retroviral replication," *Proc. Natl. Acad. Sci. USA*, 1990, 87:1874-1878
Hamm et al., "Emergency Room Triage of Patients with Acute Chest Pain by Means of Rapid Testing for Cardiac Troponin T or Troponin I," *N. Engl. J. Med.*, 1997, 337(23):1648-1653.
Haverkate et al., "Production of C-reactive protein and risk of coronary events in stable and unstable angina," *Lancet*, 1997, 349:462-466. .

(Continued)

*Primary Examiner* — Lisa V Cook
(74) *Attorney, Agent, or Firm* — Fish & Richardson P.C.

(57) ABSTRACT

Use of pregnancy-associated plasma protein-A as a marker for inflammatory conditions, and in particular, for acute coronary syndromes is described.

7 Claims, 5 Drawing Sheets

OTHER PUBLICATIONS

Huse et al., "Generation of a Large Combinatorial Library of the Immunoglobulin Repertoire in Phage Lambda," *Science*, 1989, 246:1275-1281.

Jenkins et al., "Severity of coronary atherosclerosis related to lipoprotein concentration," *Br. Med. J.*, 1978, 2:388-391.

Köhler and Milstein, "Continuous cultures of fused cells secreting antibody of predefined specificity," *Nature*, 1975, 256:495-497.

Kozbor and Roder, The production of monoclonal antibodies from human lymphocytes, *Immunology Today*, 1983, 4(3):72-79.

Kuhajda et al., "Pregnancy-associated plasma protein A. A clinically significant predictor of early recurrence in stage I breast carcinoma is independent of estrogen receptor status," *Am. J. Pathol.*, 1985, 121(2):342-348.

Kuhajda et al., "Expression of haptoglobin-related protein and its potential role as a tumor antigen," *Proc. Natl. Acad. Sci. USA*, 1989, 86:1188-1192.

Lawrence et al., "The insulin-like growth factor (IGF)-dependent IGF binding protein-4 protease secreted by human fibroblasts is pregnancy-associated plasma protein-A," *Proc. Natl. Acad. Sci. USA*, 1999, 96(6):3149-3153.

Lewis, "PCR's Competitors Are Alive and Well and Moving Rapidly Towards Commercialization," *Genetic Engineering News*, 1992, vol. 12, 3 pages.

Lin et al., "Characterization of four human pregnancy-associated plasma proteins," *Am. J. Obstet. Gynecol.*, 1974, 118(2):223-236.

Liuzzo et al., "The Prognostic Value of C-Reactive Protein and Serum Amyloid A Protein in Severe Unstable Angina," *N. Engl. J. Med.*, 1994, 331(7):417-424.

Liuzzo, "Atherosclerosis: an inflammatory disease," *Rays*, 26(4):221-230.

Lyon et al., "Minireview: adiposity, inflammation, and atherogenesis," *Endocrinology*, 2003, 144(6):2195-21200.

Meisser et al., "In vitro effects of pregnancy-associated plasman protein-A: artifacts due to heparin," *Biol. Reprod.*, 1988, 39(2):373-378.

Meisser et al., "Interaction of Pregnancy-Associated Plasma Protein-A with Coagulation A bioassay for Pregnancy-Associated Plasma Protein-A," *Biol. Reprod.*, 1985, 33(5):1073-1077.

Muller-Gartner, "Imaging techniques in the analysis of brain function and behaviour," *TIB Tech.*, 1998, 16:122-130.

Nicholas et al., "Rheumatoid arthritis and pregnancy," *Clin. Exp. Rheumatol.*, 1988, 6(2):179-182.

Overgaard et al., "Messenger Ribonucleic Acid Levels of Pregnancy-Associated Plasma Protein-A and the Proform of Eosinophil Major Basic Protein: Expression in Human Reproductive and Nonreproductive Tissues," *Biol. Reprod.*, 1999, 61:1083-1089.

Oxvig et al., "Circulating Human Pregnancy-associated Plasma Protein-A Is Disulfide-bridged to the Proform of Eosinophil Major Basic Protein," *J. Biol. Chem.*, 1993, 268(17):12243-12246.

Oxvig et al., "Identification of Angiotensinogen and Complement C3dg as Novel Proteins Binding the Proform of Eosinophil Major Basic Protein in Human Pregnancy Serum and Plasma," *J. Biol. Chem.*, 1995, 270(23):13645-13651.

Oxvig et al., "Isolation and characterization of circulating complex between human pregnancy-associated plasma protein-A and proform of eosinophil major basic protein," *Biochem. Biophys. Acta*, 1994, 1201:415-423.

Pettersson et al., "Time-resolved fluorometry (TRF)-based immunoassay concept for rapid and quantitative determination of biochemical myocardial infarction markers from whole blood, serum and plasma," *Luminescence*, 2000, 15:399-407.

Powell et al., "Serum Somatomedin Levels in Adults with Chronic Renal Failure: The Importance of Measuring Insulin-Like Growth Factor I (IGF-I) and IGF-II in Acid-Chromatographed Uremic Serum," *J. Clin. Endocrinol. Metab.*, 1986, 63(5):1186-1192.

Qin et al., "Double-monoclonal immunofluorometric assays for pregnancy-associated plasma protein A/proeosinophil major basic protein (PAPP-A/proMBP) complex in first-trimester maternal serum screening for Down syndrome," *Clin. Chem.*, 1997, 43(12):2323-2332.

Rabbani, "Acute Coronary Syndromes—Beyond Myocyte Necrosis," *N. Engl. J. Med.*, 2001, 345:1057-1059.

Saji, "Targeted Delivery of Radiolabeled Imaging and Therapeutic Agents: Bifunctional Radiopharmaceuticals," *Crit. Rev. Ther. Drug Carrier Syst.*, 1999, 16(2):209-244.

Seppala et al., "Pregnancy Proteins in Seminal Plasma, Seminal Vesicles, Preovulatory Follicular Fluid, and Ovary," *Ann. N.Y. Acad. Sci.*, 1985, 442:212-226.

Sjoberg et al., "Hyperstimulated human preovulatory follicular fluid, luteinized cells of unruptured follicles, and corpus luteum contain pregnancy-associated plasma protein a (PAPP-A)," *Fertility and Sterility*, 1984, 41(4):551-557.

Suzuki et al., "Bikunin Target Genes in Ovarian Cancer Cells Identified by Microarray Analysis," *J. Biol. Chem.*, 2003, 278(17):14640-14646.

Vaidyanathan and Zalutsky, "Improved Synthesis of N-Succinimidyl 4-[18F]Fluorobenzoate and Its Application to the Labeling of a Monoclonal Antibody Fragment," *Bioconjug. Chem.*, 1994, 5(4):352-356.

Weiss, "Hot Prospect for New Gene Amplifier," *Science*, 1991, 254:1292-1293.

European Search Report, EP Application No. 09 00 6384 mailed Jun. 23, 2009, 7 pages.

* cited by examiner

MARKER FOR INFLAMMATORY CONDITIONS

CROSS-REFERENCE TO RELATED APPLICATIONS

This application is a continuation of U.S. application Ser. No. 12/389,983, filed Feb. 20, 2009, which is a continuation of U.S. application Ser. No. 11/516,020, filed Sep. 5, 2006, which is a continuation of U.S. application Ser. No. 11/254,224, filed Oct. 18, 2005, now abandoned, which is a continuation of U.S. application Ser. No. 11/062,400 filed Feb. 22, 2005, now abandoned, which is a continuation of U.S. application Ser. No. 10/767,666, filed Jan. 29, 2004, now abandoned, which is a divisional of U.S. application Ser. No. 10/210,339, filed Jul. 31, 2002, now U.S. Pat. No. 6,699,675, which is a divisional of U.S. application Ser. No. 09/760,376, filed Jan. 12, 2001, now U.S. Pat. No. 6,500,630.

TECHNICAL FIELD

The invention relates to uses of pregnancy-associated plasma protein-A (PAPP-A) as a marker and therapeutic target for inflammatory conditions, and in particular, for acute coronary syndromes.

BACKGROUND

Pregnancy associated plasma protein-A (PAPP-A) is a high molecular weight glycoprotein originally isolated from human pregnancy serum. It is routinely used today as an index of placental function and first trimester screen for Down's syndrome. No biological function was known for PAPP-A until recent evidence linked it to the insulin-like growth factor (IGF) axis, the dynamic balance between IGF-I, IGF binding proteins (IGFBP's), and IGFBP proteases that ultimately determines the extent of IGF-dependent cellular events. PAPP-A specifically cleaves IGFBP-4, which releases IGF-I and makes it available to activate receptors. Lawrence et al. (1999) Proc. Natl. Acad. Sci. USA 96:3149-3153; and Durham et al. (1994) J. Bone Min. Res. 9:111-117.

SUMMARY

The invention is based on the use of PAPP-A levels in serum for diagnosis of inflammatory conditions, and in particular, acute coronary syndromes (unstable angina, acute myocardial infarction, sudden cardiac death, coronary plaque rupture, or thrombosis) in all stages of their occurrence. Patients with acute coronary syndromes are at considerable risk for death and serious complications, and outcomes can be improved with appropriate therapy. Thus, rapid and accurate diagnosis of chest pain is critical for patient. Also, there are important implications to predicting which patients are at risk of acute coronary syndromes before the syndrome occurs. The results described herein demonstrate that serum PAPP-A levels are elevated in unstable angina and acute myocardial infarction, are within normal ranges in stable angina, and correlate with serum levels of high-sensitivity C-reactive protein (CRP) and free IGF-I. Furthermore, PAPP-A is highly expressed in unstable plaques from sudden cardiac death patients. Thus, PAPP-A can be used as an early marker of inflammatory conditions, and in particular, acute coronary syndromes.

In one aspect, the invention features a method for diagnosing an inflammatory condition (e.g., an acute coronary syndrome such as unstable angina, sudden cardiac death, or acute myocardial infarction, rheumatoid arthritis, Crohn's disease, or inflammatory bowel disease). The method includes measuring the level of PAPP-A in a biological sample (e.g., whole blood, plasma, or serum) from a non-pregnant patient; comparing the level with that of control subjects; and diagnosing the inflammatory condition based on the level of PAPP-A relative to that of control subjects. The patient can be diagnosed as having the inflammatory condition if the level of PAPP-A is increased relative to that of control subjects. The level of PAPP-A can be measured using an immunoassay such as an ELISA. PAPP-A can be captured with anti-PAPP-A polyclonal antibodies or an anti-PAPP-A monoclonal antibody. The method further can include measuring the level of a polypeptide selected from the group consisting of high sensitivity C-reactive protein, creatine kinase MB, troponin I, troponin T, creatine kinase, creatinine, fibrinogen, interleukin-1, and interleukin-6, and diagnosing the inflammatory condition based on the level of the polypeptide and the level of PAPP-A relative to that of control subjects.

In another aspect, the invention features an article of manufacture for diagnosing an inflammatory condition in a non-pregnant patient. The article of manufacture includes an anti-PAPP-A antibody and packaging material, wherein the anti-PAPP-A antibody can be used for measuring PAPP-A levels in a biological sample (e.g., whole blood, plasma, or serum) from the patient, and wherein the packaging material includes a label or package insert indicating that the anti-PAPP-A antibody can be used for diagnosing the inflammatory condition.

In yet another aspect, the invention features an article of manufacture for diagnosing an inflammatory condition in a non-pregnant patient that includes reagents for measuring levels of a plurality of polypeptides in a biological sample from the patient. The plurality of polypeptides includes PAPP-A and one or more of the polypeptides selected from the group consisting of high sensitivity C-reactive protein, creatine kinase MB, troponin I, troponin T, creatine kinase, creatinine, fibrinogen, interleukin-1, and interleukin-6. The biological sample can be selected from the group consisting of whole blood, plasma, and serum.

The invention also features a method for diagnosing an inflammatory condition that includes administering (e.g., intravenously) to a patient an amount of an antibody having specific binding affinity for PAPP-A effective to detectably bind to PAPP-A, wherein the antibody is labeled; detecting the level of the antibody bound to PAPP-A in the patient; and diagnosing the inflammatory condition based on the level of the antibody bound to PAPP-A. The detecting step can include diagnostic imaging such as positron emission tomography, gamma-scintigraphy, single photon emission computerized tomography, magnetic resonance imaging, intravascular ultrasound, or functional magnetic resonance imaging. The label can be a radioisotope (e.g., $^{123}$I, $^{18}$F, $^{111}$In, $^{67}$Ga, and $^{99m}$Tc).

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
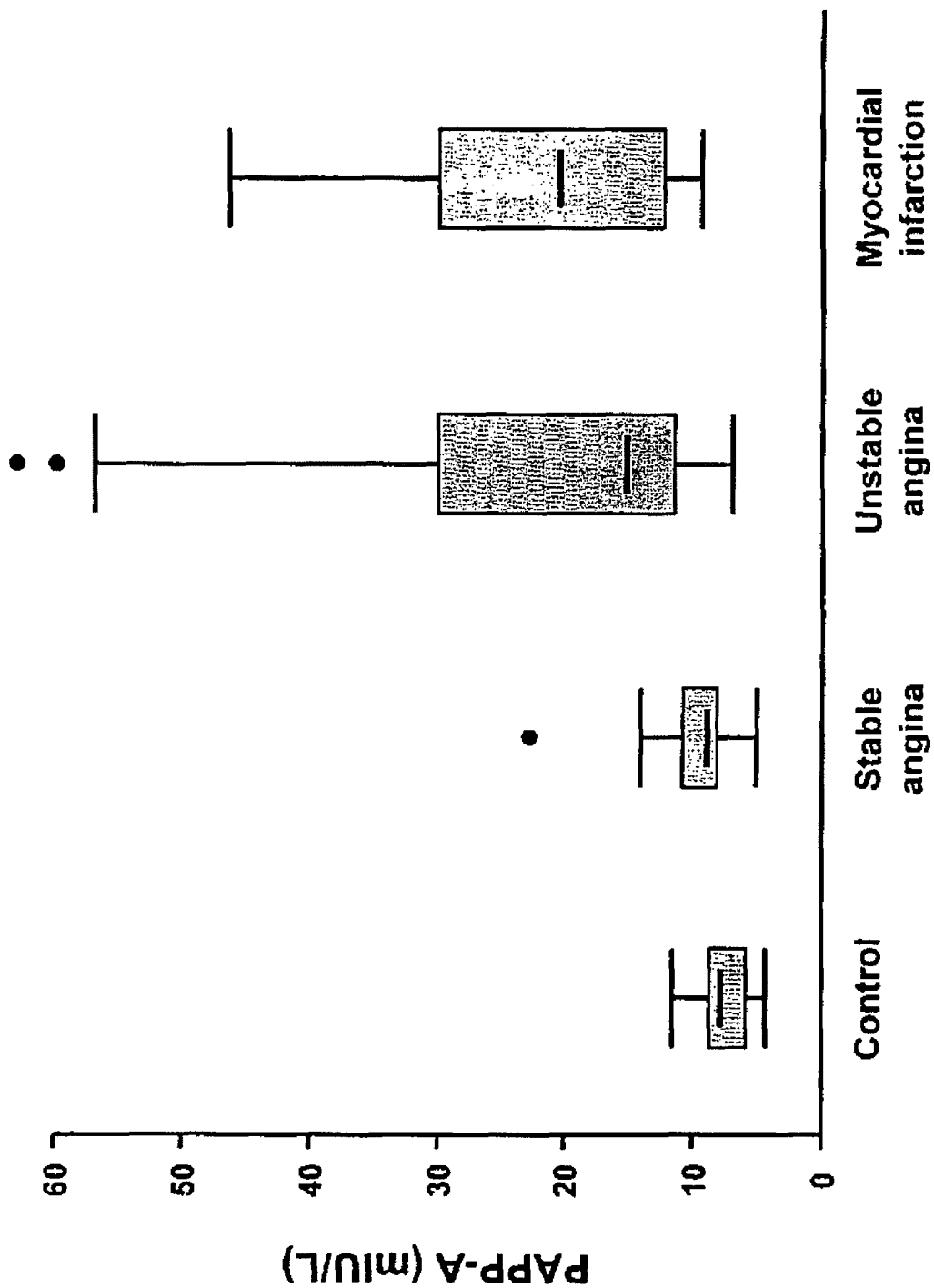
FIG. 1 is a box plot of circulating PAPP-A levels. The Kruskal-Wallis analysis for PAPP-A indicated highly significant group differences (p<0.0001).

The invention features methods for diagnosing inflammatory conditions in a mammal (e.g., a human patient), including acute and chronic inflammatory conditions, and especially those inflammatory conditions as related to vasculature. Non-limiting examples of inflammatory conditions include acute coronary syndromes (unstable angina, acute myocardial infarction, sudden cardiac death, coronary plaque rupture, or thrombosis), Crohn's disease, inflammatory bowel disease, and rheumatoid arthritis. As described herein, levels of PAPP-A are significantly higher in patients with such inflammatory conditions. For example, PAPP-A levels increase 100 fold or more in rheumatoid arthritis patients. PAPP-A levels also are significantly increased in patients with unstable angina and myocardial infarction. As raised PAPP-A levels are common in unstable angina and acute myocardial infarction and PAPP-A is up-regulated in unstable plaques from sudden cardiac death patients, PAPP-A can be used as a marker for such conditions. As described herein, PAPP-A levels above 10 mIU/L identified 17 of 20 unstable angina patients (85.0%), and 16 of 17 myocardial infarction patients (94.1%). In contrast, diagnostic sensitivities of cardiac-specific troponins and C-reactive protein in unstable angina is low. As described herein, troponin I was elevated in 3 (15%) and C-reactive protein in 10 (50%) of unstable angina patients. In other studies, only 22% of patients had a positive result for troponin T, 36% had a positive result for troponin I, and 65% had raised C-reactive protein levels. See, Hamm et al., *N. Engl. J. Med.,* 1997, 337:1648-1653 and Liuzzo et al., *N. Engl. J. Med.,* 1994, 331:417-424. Both markers, nonetheless, are associated with unfavorable outcomes when elevated. Thus, PAPP-A seems to be a valuable unstable plaque marker even when troponins and C-reactive protein are not elevated, potentially identifying high-risk patients who otherwise might remain undiagnosed. Without being bound by a particular mechanism, PAPP-A may be directly involved in the pathophysiology of acute coronary syndromes as a metalloprotease, and indirectly through release of IGF-I.

The cDNA sequence of PAPP-A indicates that the serum form is derived from a pre-proprotein with a putative 22-residue signal peptide, a pro-part of 58 residues, and a 1547-residue circulating mature polypeptide. The sequence shows no global similarity to any known protein, but it contains two sequence motifs common to the metzincins, a superfamily of metalloproteases. The sequence also contains three Lin-12/Notch repeats known from the Notch protein superfamily, and five short consensus repeats known from components of the complement system.

Inhibition of PAPP-A activity is useful for treatment of inflammatory conditions. As described herein, PAPP-A expression is strongest in the inflammatory shoulder of an unstable plaque. Therefore, inhibition of PAPP-A expression and/or proteolytic function could increase plaque stability. Without being bound by a particular mechanism, PAPP-A as a metalloprotease may be directly involved in plaque vulnerability, even before the plaque becomes clinically manifested. The proform of eosinophil major basic protein (proMBP), which is disulfide linked to PAPP-A in pregnancy serum to form an approximately 500 kDa 2:2 complex (PAPP-A/proMBP), may be useful for treating inflammatory conditions as proMBP functions as an inhibitor of PAPP-A activity.

In general, methods of the invention include measuring the level of PAPP-A in a biological sample from a non-pregnant patient and comparing the level to that from control subjects. An inflammatory condition is diagnosed based on the level of PAPP-A relative to the control. Thus, it is determined if PAPP-A levels are increased, decreased, or the same as that of control subjects. If PAPP-A levels are increased relative to that of control subjects, the diagnosis is that an inflammatory condition is present. In particular, a PAPP-A threshold value of 10 mIU/L can be used to accurately identify patients with acute coronary syndromes. The level of PAPP-A can be assessed by measuring PAPP-A protein, message (mRNA), or activity. Suitable biological samples for measuring PAPP-A levels include, for example, blood (including whole blood, plasma, and serum), urine, saliva, oral washings, and tissue biopsies such as skin, bone, or blood vessel plaque. Blood is a particularly useful biological sample.

Detection of PAPP-A Protein

PAPP-A protein can be detected, for example, immunologically. For example, a sandwich assay can be performed by capturing PAPP-A from a biological sample with an antibody having specific binding affinity for PAPP-A. PAPP-A then can be detected with a labeled antibody having specific binding affinity for PAPP-A. Alternatively, standard immunohistochemical techniques can be used to detect PAPP-A protein, using such antibodies. Antibodies having affinity for PAPP-A/proMBP complexes are available. See, for example, Qin et al., *Clin. Chem.,* 1997, 43(12):2323-2332. Monoclonal antibodies having specific binding affinity for PAPP-A, but not for PAPP-A/proMBP complexes, can be produced through standard methods.

In general, PAPP-A not complexed to proMBP can be produced in various ways, including recombinantly, or can be purified from a biological sample, and used to immunize animals. To produce recombinant PAPP-A, a nucleic acid sequence encoding PAPP-A polypeptide can be ligated into an expression vector and used to transform a bacterial or eukaryotic host cell. In general, nucleic acid constructs include a regulatory sequence operably linked to a PAPP-A nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

Mammalian cell lines that stably express PAPP-A can be produced by using expression vectors containing the appropriate control elements and a selectable marker. For example, the eukaryotic expression vector pcDNA.3.1+ (Invitrogen, San Diego, Calif.) is suitable for expression of PAPP-A in, for example, COS cells or HEK293 cells. Following introduction of the expression vector by electroporation, DEAE dextran, or other suitable method, stable cell lines are selected. In an expression system using pCDNA3.1+ and HEK293 cells, yield of the protein was about 5 μg/ml. The secreted product was a dimer devoid of proMBP. Alternatively, PAPP-A can be transcribed and translated in vitro using wheat germ extract or rabbit reticulocyte lysate.

In eukaryotic host cells, a number of viral-based expression systems can be utilized to express PAPP-A. A nucleic acid encoding PAPP-A can be cloned into, for example, a baculoviral vector and then used to transfect insect cells. Alternatively, the nucleic acid encoding PAPP-A can be introduced into a SV40, retroviral or vaccinia based viral vector and used to infect host cells.

Recombinant PAPP-A (rPAPP-A) is immunoreactive against all available monoclonal antibodies in ELISA and in Western blotting. Recombinant PAPP-A is secreted as a homodimer of about 400 kDa and, after reduction, yields monomers of about 200 kDa. rPAPP-A is active and cleaves IGFBP-4 in an IGF dependent manner. Recombinant PAPP-A is about 100-fold more active than PAPP-A/proMBP complex in pregnancy serum.

PAPP-A can be purified using standard protein purification techniques. For example, PAPP-A can be purified from conditioned media by passing over iminodiacetic acid immobilized to Sepharose 6B loaded with $Zn^{+2}$. After elution of bound proteins with a stepwise decreasing pH gradient, the pH 5.0 fraction can be purified further by passing over a wheat germ agglutinin column. Bound proteins can be eluted with a Tris-salt solution, then by N-acetylglucosamine. Alternatively, a heparin sepharose column can be used and PAPP-A is eluted with an increase in salt concentration to 1000 mM. Fractions containing PAPP-A, as measured with PAPP-A specific antibodies or with a specific protease activity assay, can be pooled, concentrated, then assessed by SDS polyacrylamide gel electrophoresis. In reducing SDS/PAGE, the molecular mass of PAPP-A monomer is approximately 200 kDa.

Various host animals can be immunized by injection of PAPP-A. Host animals include rabbits, chickens, mice, guinea pigs and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogenous populations of antibody molecules that are contained in the sera of the immunized animals. Monoclonal antibodies, which are homogeneous populations of antibodies to a particular antigen, can be prepared using a PAPP-A polypeptide and standard hybridoma technology. In particular, monoclonal antibodies can be obtained by any technique that provides for the production of antibody molecules by continuous cell lines in culture such as described by Kohler, G. et al., *Nature*, 256:495 (1975), the human B-cell hybridoma technique (Kosbor et al., *Immunology Today*, 4:72 (1983); Cole et al., *Proc. Natl. Acad. Sci USA*, 80:2026 (1983)), and the EBV-hybridoma technique (Cole et al., "Monoclonal Antibodies and Cancer Therapy", Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies of the invention can be cultivated in vitro and in vivo.

Antibody fragments that have specific binding affinity for PAPP-A polypeptide can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed. See, for example, Huse et al., *Science*, 246:1275 (1989). Once produced, antibodies or fragments thereof are tested for recognition of PAPP-A by standard immunoassay methods including ELISA techniques, radioimmunoassays and Western blotting. See, *Short Protocols in Molecular Biology*, Chapter 11, Green Publishing Associates and John Wiley & Sons, Edited by Ausubel, F. M et al., 1992. Antibodies having affinity for PAPP-A are identified in a positive selection. Antibodies identified in such a selection can be negatively selected against PAPP-A/proMBP, to identify antibodies having specific binding affinity for epitopes of PAPP-A that are not accessible in the specific complex of PAPP-A and proMBP.

Detection of PAPP-A Message

PAPP-A message can be detected, for example, by a polymerase chain reaction (PCR) assay. In general, PCR refers to amplification of a target nucleic acid, using sequence information from the ends of the region of interest or beyond to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication or nucleic acid sequence-based amplification. See, for example, Lewis, R., *Genetic Engineering News*, 12(9):1 (1992); Guatelli et al., *Proc. Natl. Acad. Sci. USA*, 87:1874-1878 (1990); and Weiss, R., *Science*, 254:1292 (1991).

For example, the levels of PAPP-A mRNA can be detected using reverse transcription-polymerase chain reaction (RT- PCR) assay. See, for example, WO 00/54806. In particular, PAPP-A cDNA can be coamplified with a deletion variant thereof that is used as an internal standard (IS). The amount of PAPP-A is normalized against the total amount of mRNA in the sample, determined as the amount of β-actin mRNA. RT-PCR has been shown to be 1,000-10,000 fold more sensitive than traditional RNA blotting techniques, and can detect and quantitate both PAPP-A and proMBP mRNA in tissue samples.

Products from competitive PCR can be quantified by ion exchange chromatography on an HPLC system, an accurate method that involves a minimum of post-PCR handling. Alternatively, real-time quantitative PCR can be performed using, for example, the ABI PRISM 7700 Sequence Detection System and Taqman fluorogenic probes, or the LightCycler™ instrument from Roche. An internal reference can be used, such as amplification of the 28S rRNA with limiting primer concentration. This method allows quantitation down to approximately 500 copies of the target sequence.

Alternatively, testing different tissues for the presence of specific mRNAs can be done routinely by RNA blotting techniques such as Northern or dot blotting or through microarray technology.

Detection of PAPP-A Activity

PAPP-A activity can be detected by examining IGFBP-4 proteolytic activity in a biological sample. For example, a detectably labeled substrate can be incubated in the presence of the biological sample under suitable conditions, and proteolytic products then are detected. The substrate can be, for example, IGFBP-4 or a fragment thereof. In general, the reaction can be carried out at 37° C. in a buffer such as 2 mM $CaCl_2$/50 mM Tris (pH 7.5), including IGF-II or fragments thereof, or any other protease activator. Typically, the substrate is labeled radioactively with isotopes such as $^{125}$I or $^{32}$P, or non-radioactively labeled with biotin, digoxygenin, or a fluorophore. Proteolysis of IGFBP-4 is detected, for example, by examining proteolysis products, such as the 18 and 14 kDa reaction products of IGFBP-4. Radioactive proteins can be separated by reducing 15% SDS/PAGE and visualized by autoradiography. Proteolytic cleavage products also can be detected by immunoblotting.

PAPP-A activity also can be detected after capturing PAPP-A with polyclonal or monoclonal antibodies immobilized, for example, in a well of a microtiter plate. After washing away unbound protein of the biological sample, the activity of PAPP-A can be measured with a low molecular weight synthetic substrate that liberates a colored product that can be detected spectrophotometrically. IGF-II or other activator of PAPP-A can be added with the substrate.

Additionally, PAPP-A activity can be detected by incubating the sample in a well that contains immobilized substrate, e.g., IGFBP-4. Substrate is specifically labeled, i.e., radioactively or non-radioactively. Upon proteolytic cleavage of the substrate, labeled fragments are liberated into the liquid phase and can be detected. Substrate can be immobilized, for example, by coating with antibodies or IGF-II.

Labeling can also be accomplished by using IGFBP-4 expressed with different tags on the N-terminus or C-terminus of the protein, for example an N-terminal FLAG tag and a C-terminal c-myc tag. This allows IGFBP-4 to be immobilized with a monoclonal antibody that binds one of these tags. Detection of bound IGFBP-4 can then be accomplished by standard ELISA methodology using, for example, a peroxidase conjugated monoclonal antibody that recognizes the other tag. IGFBP-4 can also be immobilized and detected using monoclonal antibodies that recognize the N-terminus and the C-terminus, respectively. Proteolytic activity will result in a decreased signal, dependent on the amount of proteinase activity and time of incubation.

Diagnosing Inflammatory Conditions by Visualization of PAPP-A In Vivo

Inflammatory conditions also can be diagnosed by administering an amount of an antibody having specific binding affinity for PAPP-A to a patient effective for visualizing PAPP-A in vivo. In addition, visualizing PAPP-A would allow sites in the body of abnormal accumulations, such as plaques that are potentially vulnerable, to be identified. Suitable antibodies and methods for making antibodies are described above. The antibody typically is labeled, and diagnostic imaging is used to detect antibody bound to PAPP-A. Diagnosis of the inflammatory condition is based on the increase of PAPP-A, as described above. Threshold can be set to any level, so a level over normal can be detected. Thus, diagnosis can be made based on the presence or absence of antibody bound to PAPP-A.

Typical labels that are useful include radioisotopes used for imaging procedures in humans. Non-limiting examples of labels include radioisotope such as $^{123}$I (iodine), $^{18}$F (fluorine), $^{99m}$Tc (technetium), $^{111}$In (indium), and $^{67}$Ga (gallium). Antibodies can be labeled through standard techniques. For example, antibodies can be iodinated using chloramine T or 1,3,4,6-tetrachloro-3α,6α-diphenylglycouril. Antibodies can be labeled with $^{18}$F through, for example, N-succinimidyl 4-[$^{18}$F]fluorobenzoate. See, Muller-Gartner, H., *TIB Tech.*, 16:122-130 (1998); Saji, H., *Crit. Rev. Ther. Drug Carrier Syst.*, 16(2):209-244 (1999); and Vaidyanathan and Zalutsky, *Bioconjug. Chem.* 5(4):352-6 (1994) for a review of labeling of antibodies with such radioisotopes.

The labeled antibodies are formulated with a pharmaceutically acceptable carrier and administered to the patient. In general, the antibodies are administered intravenously (i.v.), although other parenteral routes of administration, including subcutaneous, intramuscular, intrarterial, intracarotid, and intrathecal also can be used. Formulations for parenteral administration may contain pharmaceutically acceptable carriers such as sterile water or saline, polyalkylene glycols such as polyethylene glycol, vegetable oils, hydrogenated naphthalenes, and the like.

The dosage of labeled antibody to be administered will be determined by the attending physician taking into account various factors known to modify the action of drugs. These include health status, body weight, sex, diet, time and route of administration, other medications, and any other relevant clinical factors.

Imaging techniques that can be used to detect PAPP-A in vivo include positron emission tomography (PET), gamma-scintigraphy, magnetic resonance imaging (MRI), functional magnetic resonance imaging (FMRI), single photon emission computerized tomography (SPECT), and intravascular ultrasound.

Articles of Manufacture for Diagnosing Inflammatory Conditions

Antibodies having specific binding affinity for PAPP-A can be combined with packaging material and sold as a kit for diagnosing inflammatory conditions. Components and methods for producing articles of manufactures are well known. The articles of manufacture may combine one or more anti-PAPP-A antibodies or fragments thereof as described herein. In addition, the articles of manufacture may further include reagents for measuring levels of a plurality of polypeptides in a biological sample, including, for example, antibodies having specific binding affinity to the particular polypeptide, secondary antibodies, indicator molecules, solid phases (e.g., beads) and/or other useful agents for diagnosing inflammatory conditions. Instructions describing how the various reagents are effective for diagnosing inflammatory conditions also may be included in such kits. Polypeptides that may be useful to measure in combination with PAPP-A include polypeptide markers of inflammation, markers correlating with increased risk of unstable angina or myocardial infarction (e.g., homocysteine), markers of cardiac injury, and other non-specific markers of inflammation. For example, interleukin-1 (IL-1), IL-6, or neopterin can be assessed in combination with PAPP-A as a marker for inflammation. Cardiac markers and non-specific markers of inflammation include, for example, troponin I or T, hs-CRP, creatine kinase (CK), CK-MB, creatinine, myoglobin, and fibrinogen.

Particular combinations of polypeptides that can be used for diagnosing a patient with acute coronary syndrome include, for example, PAPP-A, troponin I, and CK-MB; PAPP-A, troponin I, and hs-CRP; PAPP-A, CK-MB, and myoglobin; PAPP-A and myoglobin; PAPP-A and hs-CRP; PAPP-A and troponin I or T; and PAPP-A and CK-MB. In general, myoglobin is not cardiac specific, but is released from infarcted myocardium at an early stage (about 2-3 hours post infarction) and returns to normal within about 24 hours. Cardiac isoforms of troponin I and troponin T are specific, but appear in the circulation later than myoglobin (5 to 48 hours post infarction). Myocardial tissue contains one isoform of CK-MB, while skeletal tissue has different isoforms. Antibodies having specific binding affinity for such cardiac markers are available commercially.

The anti-PAPP-A antibody can be in a container, such as a plastic, polyethylene, polypropylene, ethylene, or propylene vessel that is either a capped tube or a bottle. Non-limiting examples of other reagents that can be included in the kit are, for example, labeled, secondary antibodies that bind to the anti-PAPP-A antibody and buffers for washing or detecting PAPP-A. Reagents for measuring levels of other polypeptides can be included in separate containers or can be included on a solid phase with anti-PAPP-A antibody, e.g., a handheld device for bedside testing that includes anti-PAPP-A antibody and one or more antibodies having specific binding affinity for markers of inflammation or in particular, cardiac injury.

The invention will be further described in the following examples, which do not limit the scope of the invention described in the claims.

EXAMPLES

Example 1

Methods and Materials

Patient population: The study groups consisted of 17 patients with acute myocardial infarction, 20 with unstable angina, 19 with stable angina, and 13 age-matched control patients without clinical or angiographic evidence of coronary atherosclerosis. Acute myocardial infarction was defined as prolonged chest pain accompanied by ST-T segment elevation or depression evolving into pathologic Q-wave or T-wave inversion confirmed by an elevation of CK-MB fraction of more than twice the upper limit of normal, and troponin I>0.5 ng/mL. Unstable angina was defined as rest chest discomfort with either ST-T segment depression (greater than or equal to 0.1 mV) or T-wave inversion in 2 or more contiguous electrocardiographic leads, CK-MB fraction within normal limit, and angiographically proven coronary artery disease. Chronic stable effort angina was diagnosed as chest pain of at least six months duration, evidence of severe coronary artery disease at coronary angiography, and no clinically evident ischemic episodes during the previous week. Exclusion criteria were advanced kidney or liver failure, overt heart failure, and major surgery or trauma within the previous month. Patients with known or suspected systemic thrombotic disorders (other than from coronary origin), inflammatory diseases, or pregnancy were also excluded. Angiographic severe coronary artery disease was defined as one or more stenosis with a diameter reduction $\geq$70% in any major coronary artery. To identify a possible association between PAPP-A levels and the extent and severity of coronary artery disease discovered at angiography, the Jenkins score was obtained from every patient. Jenkins et al., *Br. Med. J.*, 1978, 2:388-391. Blood samples were taken at coronary angiography, placed on ice and centrifuged within 30 minutes at 1600 G for 5 minutes. All samples were analyzed without knowledge of the clinical data. The mean time from the last ischemic episode to blood sampling was 8.4±3 hours in myocardial infarction and 9.4±3.9 hours in unstable angina.

The study was approved by the Institutional Review Board of the Mayo Clinic and Foundation, and all patients gave informed consent.

Human Tissue and Analysis: Atherosclerotic arteries were collected at autopsy from 8 patients within 24 hours of sudden death. Sudden cardiac death was defined as described by Burke et al., *N. Engl. J. Med.*, 1997, 336:1276-1282. Acute plaque rupture, plaque erosion, and stable plaque characteristics were also defined as described by Burke et al., supra.

Immunohistochemical staining was performed on 5-mm-thick paraffin sections using a peroxidase-labeled streptavidin-biotin method. Slides were deparaffinized and rehydrated through the following solutions: xylene twice for 5 minutes, 100% ethanol twice for 1 minute and 95% ethanol twice for 1 minute. Endogenous peroxidase activity was blocked ten minutes room temperature (RT) in 1.5% $H_2O_2$/50% methanol and rinsed in running tap water. Non-specific protein binding sites were blocked by applying 5% normal goat serum diluted in PBS/0.05% Tween 20 (pH=7.2-7.4) to slides for ten minutes RT. The serum was blotted off and the primary antibody at indicated dilutions was applied and incubated one-hour RT in a humidity chamber. The primary antibody was rinsed in tap $H_2O$ and blotted, then biotinylated goat anti mouse IgG, diluted 1/400, was incubated on the slides for 30 minutes RT. Slides were rinsed in running tap H2O, blotted, and streptavidin-horseradish peroxidase diluted 1/500 in PBS/0.05% Tween20+1% normal goat serum was applied and incubated 30 minutes RT. The slides were developed with 3-amino-9-ethylcarbazole (AEC) and counterstained with hematoxylin. Monoclonal human PAPP-A antibody (234-5) was used at a concentration of 20 mg/mL (Qin et al., *Clin. Chem.* 1997, 43:2323-32). Sections were also stained with antibodies to α-smooth muscle actin (clone 1A4, Dako; 1/50) or antibodies to macrophage CD68 (clone KP-1, Dako; 1/200). Negative controls were stained by omitting the primary antibody. Total plaque area and the percentage of plaque area that stained for PAPP-A were evaluated. Quantitative analysis of immunohistochemistry was performed using a quantitative color image analysis system (Diagnostic Instruments, Inc., Sterling Heights, Mich.).

Laboratory Assays: PAPP-A was measured by a sandwich biotin-tyramide amplified ELISA (sensitivity 0.03 mIU/L;

units from WHO IRP 78/610) using PAPP-A polyclonal antibodies for capturing and a combination of PAPP-A monoclonal antibodies for detection. See, Oxvig et al. (1994) *Biochim. Biophys. Acta* 1201:415-423 and Qin et al. (1997) *Clin. Chem.* 43:2323-2332 for a description of the polyclonal and monoclonal antibodies, respectively.

The quantitative determination of CRP was achieved by latex particle enhanced immunoturbidimetric assay (Kamiya Biomedical Corp., Seattle, Wash.). Latex particles coated with antihuman CRP antibodies aggregate in the presence of serum CRP forming immune complexes. The formed immune-complexes cause increased turbidity (measured at 572 nm) that is proportional to the concentration of CRP in the serum.

Total IGF-I was measured by a commercially available assay (DSL-5600 Active IGF-I, Diagnostic Systems Laboratories Inc., Webster, Tex.). Assay of plasma IGF-I is complicated by the presence of IGF-binding proteins, which may sequester IGF-I in the reaction mixture. Daughaday and Rotwein (1989) *Endocrin. Rev.* 10:68-91. The procedure employs a two-site immunoradiometric assay (IRMA) including a simple extraction step in which IGF-I is separated from its binding protein in serum. Powell et al. (1986) *J. Clin. Endocrinol. Metab.* 63:1186-1192. Free IGF-I was assayed by a commercially available coated-tube IRMA kit (DSL-9400 Active free IGF-I, DSL Inc., Webster, Tex.). The free IGF-I IRMA is a non-competitive assay used to measure the dissociable fraction of IGF-I. Frystyk et al. (1994) 348:185-191.

CK-MB isoenzyme and cardiac troponin I (cTnI) were measured with an immunochemiluminometric assay (Chiron Corp, Emeryville, Calif.).

Statistical Analysis: Histologic data are presented as mean±SD. Eroded and ruptured plaques were compared to stable plaques by means of student's t test. Differences in demographic and angiographic characteristics between groups were compared using analysis of variance or two-way cross-tabulation with $\chi 2$ when appropriate. Data on PAPP-A, free-IGF-I, total IGF-I, and C-reactive protein, which were not distributed normally, were summarized by medians and box plots, and compared among groups by the Kruskal-Wallis test. When this showed significant group differences, pairwise group comparisons were made using the Wilcoxon rank sum statistic. Associations among circulating levels of these proteins were assessed by Spearman's rank correlation coefficient. Associations of PAPP-A with patient risk factors, and group comparisons of PAPP-A adjusted for these risk factors, were assessed using multiple linear regression with logarithm of PAPP-A as the dependent variable. Receiver operating characteristic (ROC) analysis was performed on PAPP-A and C-reactive protein for myocardial infarction and unstable angina. The areas under the curve were compared between PAPP-A and C-reactive protein by the method of DeLong et al. (*Biometrics*, 1988, 44:837-845). P values less than 0.05 were considered statistically significant.

Example 2

Tissue PAPP-A Expression in Unstable Plaques

Four ruptured plaques and four plaque erosions were identified as the culprit unstable plaques in the autopsy series. Four stable plaques were also characterized. No statistically significant differences in plaque burden were identified between ruptured ($7.1 \pm 1.4$ mm$^2$), eroded ($8.0 \pm 3.7$ mm$^2$), and stable plaques ($5.7 \pm 2.1$ mm$^2$). In plaques with large lipid cores and cap rupture, PAPP-A stained mostly in the inflammatory shoulder region, in areas surrounding the lipid core, and co-localized with CD68-positive cells. In fibrous plaques with superficial erosion, PAPP-A was identified within spindle-shaped smooth muscle cells, in the extracellular matrix, and in non-eroded endothelial cells. By quantitative image analysis, PAPP-A expression in fibrous eroded plaques ($28.3 \pm 16.8\%$) exceeded that in ruptured plaques ($18.5 \pm 8\%$), without reaching statistical significance (p=0.34). PAPP-A was only minimally expressed in stable plaques. By quantitative analysis, PAPP-A expression in stable plaques ($3.2 \pm 1.9\%$) was significantly lower than ruptured (p=0.01) and eroded plaques (p=0.02).

Example 3

Circulating Marker Proteins in Acute Coronary Patients

To determine whether abundant PAPP-A tissue expression in unstable plaques would translate to elevated circulating levels, PAPP-A levels were measured in patients with acute coronary syndromes (myocardial infarction and unstable angina) and in stable patients (stable angina and non-atherosclerotic controls). Table 1 shows age, sex, risk factor profile, baseline therapy, and angiographic results of the four studied groups. Patients with stable angina had three vessel disease more often than myocardial infarction patients (p=0.004), but no statistical differences were observed among the three diseased groups (stable angina, unstable angina, and myocardial infarction) regarding coronary atherosclerotic burden evaluated by the angiographic Jenkins score (p=0.88). Normal controls tended to have lower levels of the various risk factors than the three disease groups, but the three groups were comparable amongst themselves.

Group data on PAPP-A levels are shown as box plots in FIG. 1. The Kruskal-Wallis test indicated highly significant group differences (p<0.0001). Median serum PAPP-A levels in control patients were 7.4 mIU/L (range 3.8 to 11.3 mIU/L), and not significantly different from those observed in stable angina (median 8.3 mIU/L; range 4.4 to 22.5 mIU/L) (p=0.068). In unstable angina, median PAPP-A levels were 15.0 IU/L (range 4.4 to 22.5 mIU/L), significantly higher than those observed for control (p<0.0001) and stable angina patients (p=0.0002). In acute myocardial infarction, PAPP-A levels were 20.6 mIU/L (range 9.2 to 46.6 mIU/L), significantly higher than those observed for control (p<0.0001) and stable angina patients (p<0.0001). Distribution of PAPP-A was not significantly different between unstable angina and myocardial infarction patients (p=0.75). In this study, troponin I and CK-MB levels were not associated with PAPP-A in patients with acute coronary syndromes, indicating that PAPP-A response is not induced by myocardial necrosis.

Using multiple regression models, PAPP-A levels were not associated with age, sex, risk factors or medications. Among the three disease groups, PAPP-A levels were significantly inversely associated with atherosclerosis evaluated as number of vessels with significant lumen stenosis (1- to 3-vessel disease) (p=0.037), but were not associated with the Jenkins score (p=0.27). This reflects the coexistence in the coronary tree of quiescent atherosclerotic plaques with active, vulnerable or fissured plaques.

TABLE 1

Demographic and angiographic characteristics of control patients and patients with stable angina, unstable angina, and acute myocardial infarction

|  | Control (n = 13) | Stable Angina (n = 19) | Unstable Angina (n = 20) | Myocardial Infarction (n = 17) |
| --- | --- | --- | --- | --- |
| Age, y (mean ± SD) | 58.5 ± 13.2 | 66.4 ± 10.9 | 67.7 ± 11.7 | 63.4 ± 10.4 |
| Sex, M/F | 5/8 | 15/4 | 13/7 | 10/7 |
| Risk factors, n (%) | | | | |
| Hypertension | 4 (30.8) | 9 (47.4) | 6 (30) | 8 (47) |
| Smokers | 0 (0) | 4 (21) | 6 (30) | 5 (29.4) |
| Hypercholesterolemia | 2 (15.4)* | 12 (63.1) | 13 (65) | 11 (64.7) |
| Diabetes | 0 (0) | 6 (31.6) | 6 (30) | 2 (11.8) |
| Therapy, n (%) | | | | |
| Aspirin | 3 (23.1)* | 17 (89.5) | 18 (90) | 16 (94.1) |
| β-blocker | 3 (23.1)* | 15 (79) | 13 (65) | 13 (76.5) |
| ACE Inhibitors | 1 (7.7)* | 2 (10.5)** | 10 (50) | 7 (41.2) |
| Nitrates | 1 (7.7) | 2 (10.5) | 4 (20) | 1 (5.9) |
| Statins | 2 (15.4)* | 13 (68.4) | 13 (65) | 11 (64.7) |
| Calcium channel blockers | 2 (15.4)* | 8 (42.1) | 6 (30) | 0 (0)** |
| Angiography, n (%) | | | | |
| 1-vessel disease | 0 (0)* | 4 (21.1) | 6 (30) | 7 (41.2) |
| 2-vessel disease | 0 (0)* | 4 (21.1) | 7 (35) | 8 (47.1) |
| 3-vessel disease | 0 (0)* | 11 (57.9) | 7 (35) | 2 (11.8)** |
| Jenkins Score, mean ± SD | 0* | 13.3 ± 6.8 | 13.2 ± 9.9 | 12.1 ± 4.9 |

CRP levels were measured to assess the relation of PAPP-A to
*Significant vs. the three atherosclerotic groups (p < 0.05);
**Significant vs. other atherosclerotic groups (p < 0.05) inflammation.

Figure 2:
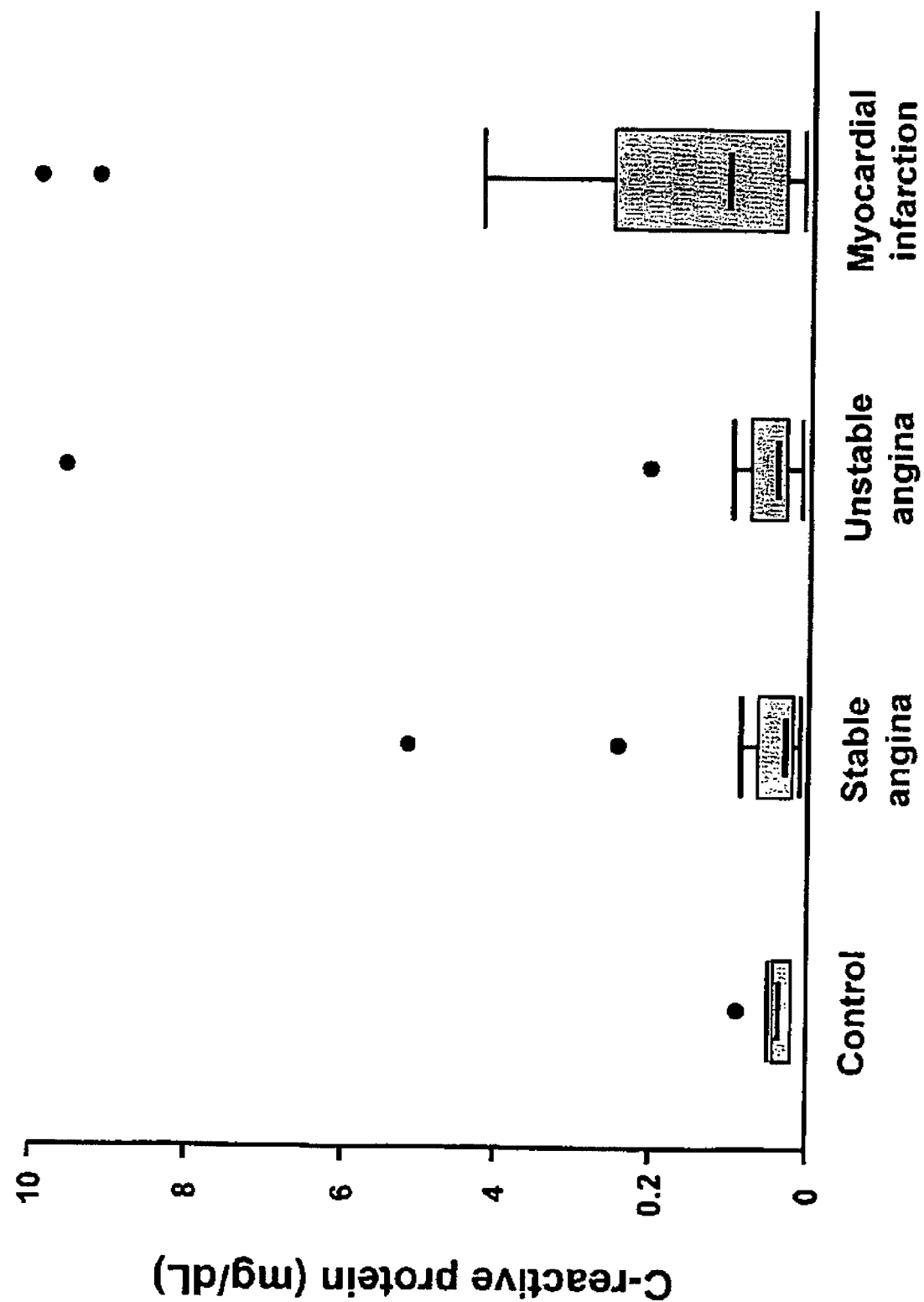
FIG. 2 is a graph of C-reactive protein levels in the four studied groups: non-atherosclerotic controls, stable angina, unstable angina and acute myocardial infarction. The Kruskal-Wallis analysis for C-reactive protein indicated highly significant group differences (p=0.0015).
Figure 3:
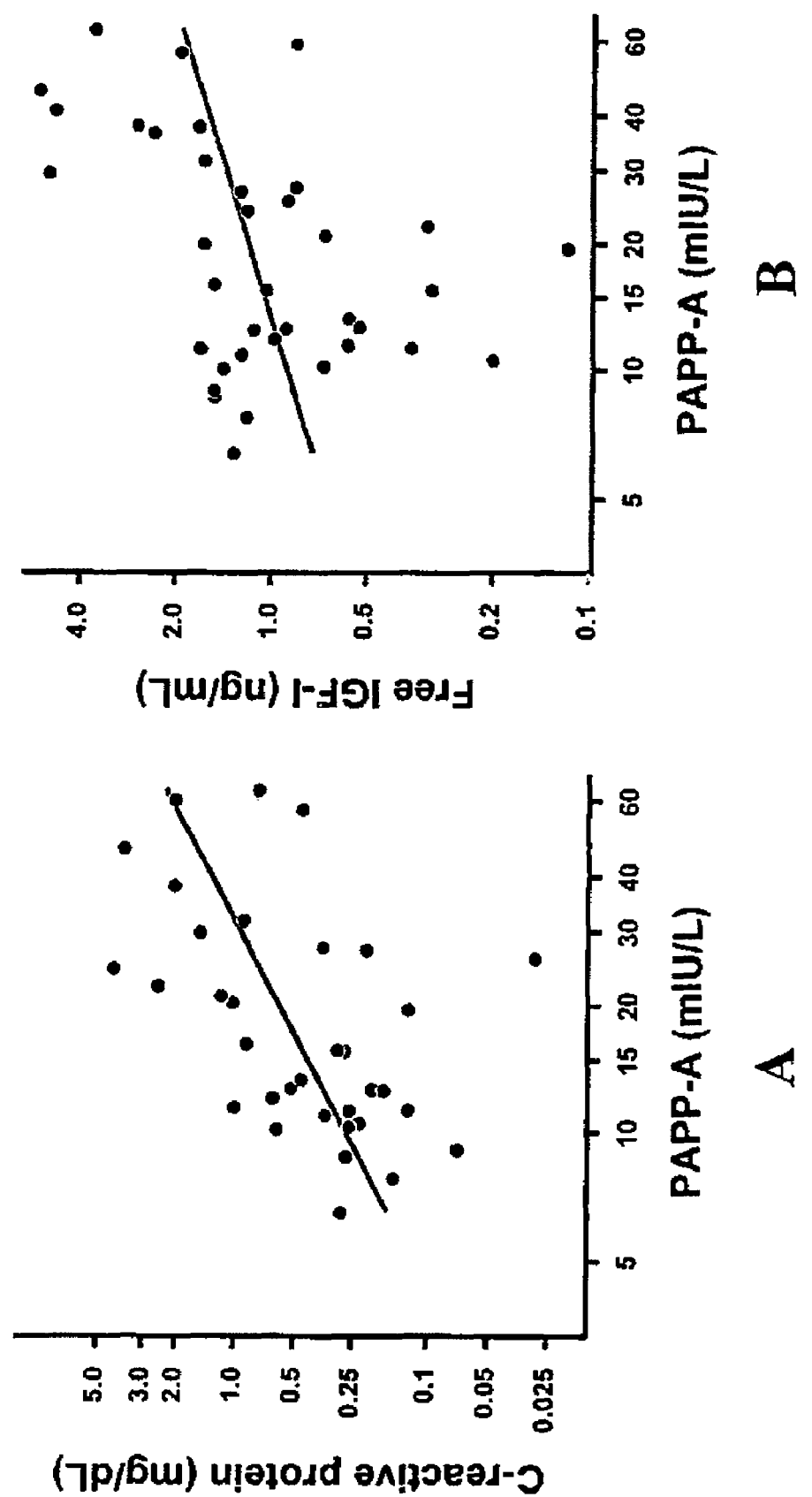
FIGS. 3A and 3B are graphs of the correlation between PAPP-A and C-reactive protein (3A), and between PAPP-A and free IGF-I levels (3B) in patients with acute coronary syndromes (n=37). A significant association was found between PAPP-A and C-reactive protein ($\rho=0.61$, p<0.001), and with free-IGF-I ($\rho=0.39$, p=0.018).

The Kruskal-Wallis analysis for CRP indicated highly significant group differences (p=0.0015). CRP levels were significantly elevated in myocardial infarction compared to unstable and stable angina patients (p=0.018 and p=0.001, respectively) (FIG. 2), and were slightly but significantly elevated in unstable compared to stable angina patients (p=0.0445)(Table 2). Control group CRP levels were only significantly lower than myocardial infarction levels (p=0.0057). CRP was significantly associated with PAPP-A in patients with acute coronary syndromes ($\rho$=0.61, p<0.0001) (FIG. 3A). CRP levels were not associated with age, sex, risk factors, medications, or coronary atherosclerotic burden.

The significant correlation between PAPP-A and CRP shows that all patients with acute coronary syndromes and hs-CRP levels >0.3 ng/mL (levels associated with increased risk of developing myocardial infarction [see, Haverkate et al., (1997) Lancet, 349:462-466) had elevated PAPP-A levels >8.9 mIU/L. However, 13 patients with acute coronary syndromes (35.1%) (5 myocardial infarction patients and 8 unstable angina patients) showed CRP levels <0.3 ng/mL and high PAPP-A levels.

Free-IGF-I was measured to determine the bioactive circulating level of IGF-I. It was hypothesized that increased PAPP-A levels would yield increased free IGF-I levels by IGFBP-4 proteolysis. No statistical differences in free IGF-I levels were found between groups, but a weak, yet significant, correlation was observed with PAPP-A levels ($\rho$=0.39; p=0.018; FIG. 3B) in patients with acute coronary syndromes. The free fraction of circulating and locally synthesized IGF-I induces vascular smooth muscle cell migration, and is important for monocyte chemotaxis, activation and cytokine release within the atherosclerotic lesion. No differences were found for total IGF-I levels between unstable and stable patients, and no association with PAPP-A levels was observed (Table 2).

CK-MB levels were not increased in blood samples obtained from unstable angina patients, and only 3 of 20 patients with unstable angina had troponin I levels above normal (1.6±0.7 ng/mL). Peak troponin I and CK-MB levels in myocardial infarction patients rose to 60.9 ng/mL (range, 1.3 to 368 ng/mL) and 76.3 ng/mL (range, 4.4 to 341 ng/mL), respectively. In these patients, there were no significant correlations between troponin I ($\rho$=0.34; p=0.19) or CK-MB

TABLE 2

Median (range) for CRP, free-IGF-I and total IGF-I levels in control patients and patients with stable angina (SA), unstable angina (UA), and acute myocardial infarction (MI)

|  | Control (n = 13) | SA (n = 19) | UA (n = 20) | MI (n = 17) |
| --- | --- | --- | --- | --- |
| CRP (mg/dL)* | 0.28 (0.08-0.8) | 0.16 (0.02-5.2) | 0.3 (0.03-9.7) | 1.03 (0.07-9.9) |
| Free-IGF-I (ng/mL) | 0.9 (0.3-3.9) | 0.78 (0.4-1.7) | 1.2 (0.1-3.5) | 1.18 (0.2-5.2) |
| Total IGF-I (ng/mL) | 108.8 (45.1-374.3) | 151.2 (60.2-262.4) | 141.3 (21.6-317.2) | 112.5 (12.4-251) |

Figure 4:
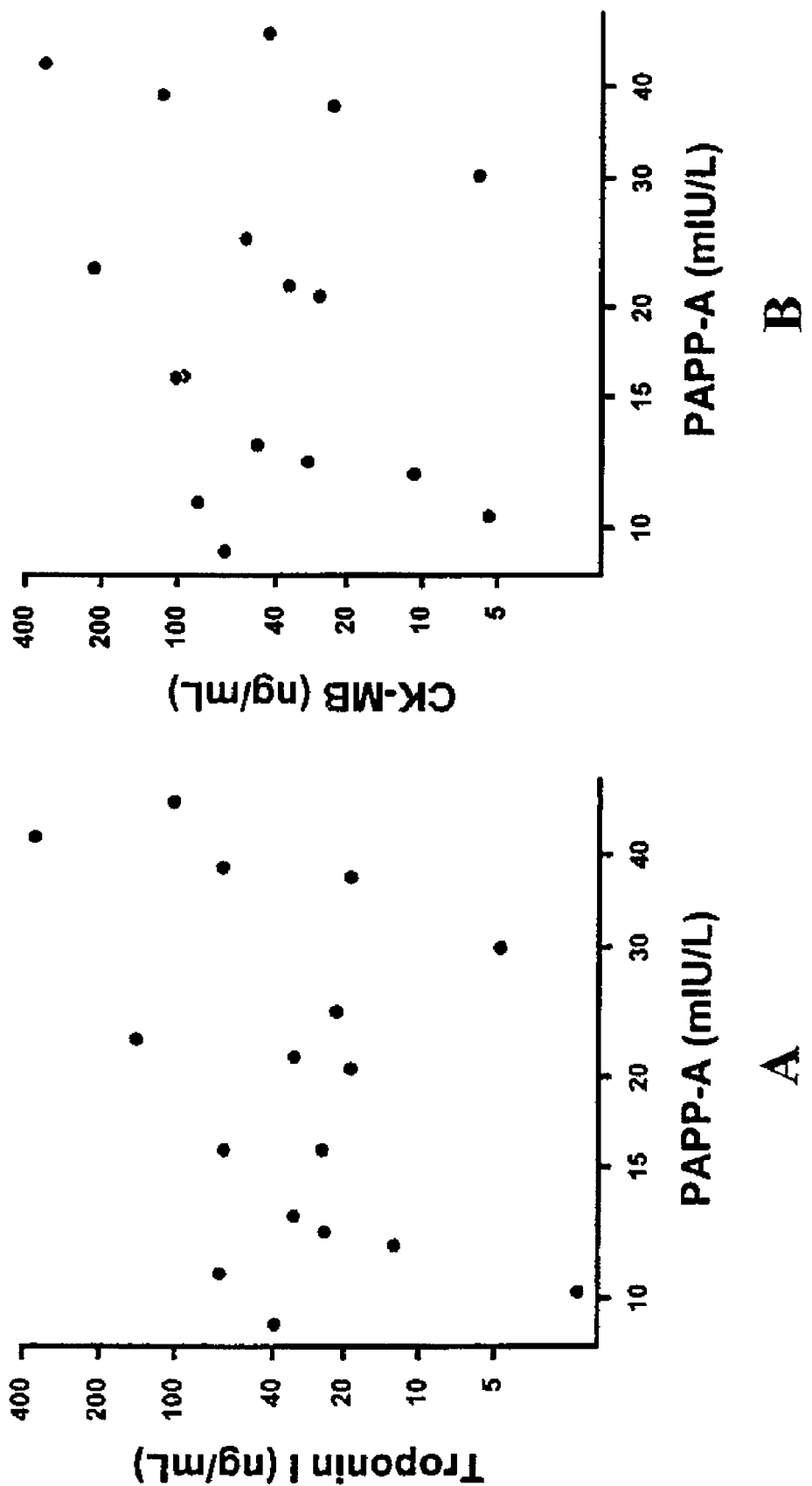
FIGS. 4A and 4B are graphs of the correlation between PAPP-A levels and the cardiac necrosis markers troponin I (4A) and CK-MB (4B) in patients with acute myocardial infarction. No significant association was found between troponin I ($\rho=0.33$, p=0.18) or CK-MB ($\rho=0.23$, p=0.36) and PAPP-A levels.

*p = 0.0015 among groups ($\rho$=0.24; p=0.36) and PAPP-A levels (FIGS. 4A and 4B). Even when unstable angina and myocardial infarction patients were combined, there was no significant association between troponin I ($\rho$=0.07, p=0.69) or CK-MB ($\rho$=0.10, p=0.57) and PAPP-A levels. Therefore, the elevated PAPP-A levels in these patients cannot be attributed to myocardial necrosis.

Example 4

PAPP-A as a Diagnostic Marker of Acute Coronary Syndromes

Figure 5:
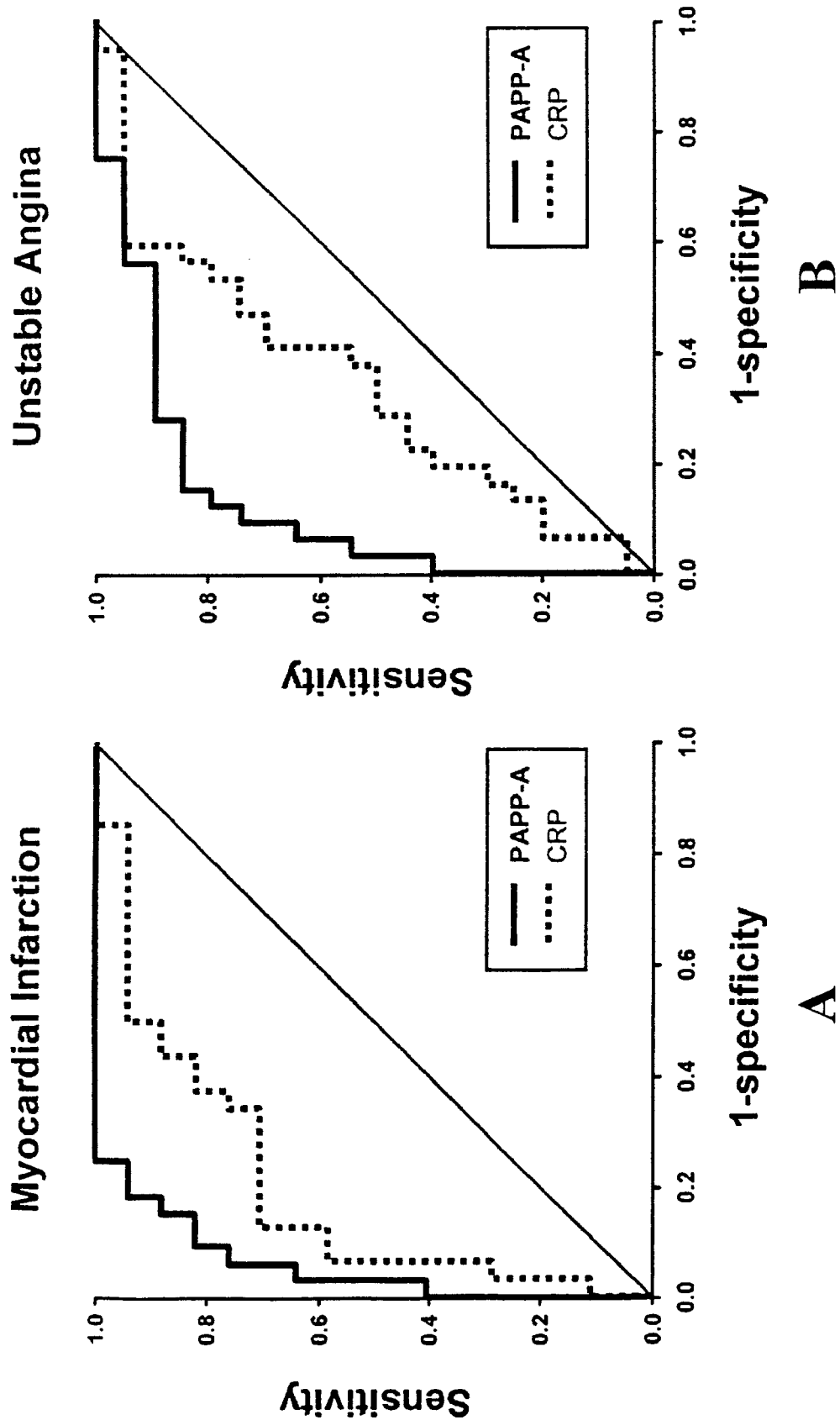
FIGS. 5A and 5B are graphs of the receiver operating characteristic (ROC) analysis of PAPP-A and C-reactive protein in patients with acute myocardial infarction (5A) and unstable angina (5B). The area under the curve (AUC) of PAPP-A was 0.94 in acute myocardial infarction (standard error=0.03), and 0.88 (standard error=0.05) in unstable angina. Statistically significant differences in AUCs were found between the two markers for acute myocardial infarction (p=0.026) and unstable angina (p=0.011). CRP=C-reactive protein.

The area under the curve (AUC) of ROC analysis for PAPP-A was 0.94 in myocardial infarction (standard error=0.03), and 0.88 (standard error=0.05) in unstable angina, pooling stable angina and control patients as the stable group. In a parallel analysis, C-reactive protein had an AUC of 0.81 (standard error=0.07) in myocardial infarction, and of 0.67 (standard error=0.08) in unstable angina. These differences in AUCs between the two markers were significant both for myocardial infarction (p=0.026) and for unstable angina (p=0.011) (FIGS. 5A and 5B, respectively). These data suggest that PAPP-A is a valuable marker, significantly better than C-reactive protein, for the identification of patients with acute coronary syndromes.

The discriminant power (combined sensitivity and specificity) for acute coronary syndromes was best at PAPP-A levels of 10 mIU/L. The sensitivity and specificity of PAPP-A levels >10 mIU/L to identify acute coronary syndromes were 89.2% and 81.3%, respectively. For myocardial infarction, the sensitivity of PAPP-A levels >10 mIU/L was 94.1% and for unstable angina 85.0%, respectively. In non-atherosclerotic controls only 1 of 13 patients (7.7%) showed PAPP-A levels >10 mIU/L, and 5 of 19 patients (26.3%) with stable angina had PAPP-A levels >10 mIU/L.

Example 5

PAPP-A Levels in Rheumatoid Arthritis Patients

PAPP-A levels were assessed in serum samples from 16 patients with Rheumatoid Arthritis. Values ranged from 3 to >2000 mIU/ml. In 13 of 16 patients, PAPP-A levels were >119 mIU/ml (119 to >2000). For comparison, normal subjects (n=30) have a PAPP-A level of 4.32±1.54 mIU/ml). Table 3 contains the individual values for the 16 rheumatoid arthritis patients.

TABLE 3

| PAPP-A Levels in Rheumatoid Arthritis Patients (mIU/ml) | | | |
|---|---|---|---|
| 3 | 759 | 592 | 253 |
| 14 | >2000 | 377 | >2000 |
| 119 | >2000 | 905 | 308 |
| 188 | 192 | 572 | 16 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence an unstable plaque in a non-pregnant subject, said method comprising:
    a) measuring the level of pregnancy-associated plasma protein-A (PAPP-A) in a biological sample from said non-pregnant subject;
    b) comparing said level with that of control subjects; and
    c) detecting said unstable plaque based on the level of PAPP-A relative to that of control subjects, wherein said unstable plaque is detected if the level of PAPP-A is increased relative to that of control subjects.

2. The method of claim 1, wherein said level of PAPP-A is measured using an immunoassay.

3. The method of claim 2, wherein said immunoassay is an ELISA.

4. The method of claim 3, wherein PAPP-A is captured using anti-PAPP-A polyclonal antibodies.

5. The method of claim 3, wherein PAPP-A is captured using anti-PAPP-A monoclonal antibodies.

6. The method of claim 1, wherein said biological sample is selected from the group consisting of whole blood, plasma, and serum.

7. The method of claim 1, wherein said biological sample is a plaque.

* * * * *

UNITED STATES PATENT AND TRADEMARK OFFICE
CERTIFICATE OF CORRECTION

PATENT NO. : 7,939,280 B2
APPLICATION NO. : 12/785893
DATED : May 10, 2011
INVENTOR(S) : Cheryl A. Conover Page 1 of 1

It is certified that error appears in the above-identified patent and that said Letters Patent is hereby corrected as shown below:

Title Page,
Column 2 (other publications), line 45, before "human" delete "1994, 348:185-191".

Column 16, line 23 (Claim 1), after "presence" insert --of--.

Signed and Sealed this
Twenty-second Day of November, 2011

David J. Kappos
*Director of the United States Patent and Trademark Office*